United States Patent
Icoz et al.

(10) Patent No.: US 12,285,036 B2
(45) Date of Patent: Apr. 29, 2025

(54) BINDING SYRUP COMPOSITION COMPRISING ALLULOSE AND LOW SUGAR SYRUPS, PRODUCTS CONTAINING THE SYRUP COMPOSITION AND METHODS OF MAKING

(71) Applicant: CORN PRODUCTS DEVELOPMENT, INC., Westchester, IL (US)

(72) Inventors: Didem Icoz, Bridgewater, NJ (US); Matthew Park, Bridgewater, NJ (US)

(73) Assignee: Corn Products Development, Inc., Westchester, IL (US)

( * ) Notice: Subject to any disclaimer, the term of this patent is extended or adjusted under 35 U.S.C. 154(b) by 596 days.

(21) Appl. No.: 17/609,520

(22) PCT Filed: Apr. 24, 2020

(86) PCT No.: PCT/US2020/029700
§ 371 (c)(1),
(2) Date: Nov. 8, 2021

(87) PCT Pub. No.: WO2020/226909
PCT Pub. Date: Nov. 12, 2020

(65) Prior Publication Data
US 2022/0211090 A1  Jul. 7, 2022

Related U.S. Application Data (60) Provisional application No. 62/844,829, filed on May 8, 2019, provisional application No. 62/895,253, filed on Sep. 3, 2019.

(51) Int. Cl.
*A23L 29/30* (2016.01)
*A23L 7/126* (2016.01)

(52) U.S. Cl.
CPC ............ *A23L 29/30* (2016.08); *A23L 7/126* (2016.08); *A23V 2002/00* (2013.01)

(58) Field of Classification Search
CPC .................. A23L 29/30; A23L 7/126
See application file for complete search history.

(56) References Cited

U.S. PATENT DOCUMENTS

| | | |
|---|---|---|
| 2015/0072065 A1 | 3/2015 | Hoffman et al. |
| 2016/0015065 A1 | 1/2016 | Sumner et al. |

(Continued)

FOREIGN PATENT DOCUMENTS

| | | |
|---|---|---|
| EP | 3427599 A1 | 1/2019 |
| JP | 2019-505219 A2 | 2/2019 |

(Continued)

*Primary Examiner* — Katherine D Leblanc (57) ABSTRACT

A binding syrup composition for formulating food products containing allulose and low sugar syrups is provided. The binding syrup composition overcomes limitations of allulose-containing products including product stickiness and failure to maintain shape and texture of the products. More particularly, the binding syrup compositions described herein contain low sugar syrups with low mono- and di-saccharide content in combination with allulose to provide binding and textural attributes to the allulose-containing food products that are comparable to full sugar products. Food products containing the allulose binding syrup compositions described herein and methods of making the same are also provided. Beneficially, food products having reduced caloric and sugar content are provided when employing the allulose-containing binding syrup compositions described herein.

14 Claims, 1 Drawing Sheet

(56) References Cited

U.S. PATENT DOCUMENTS

| | | |
|---|---|---|
| 2016/0331014 A1 | 11/2016 | Perera |
| 2017/0318850 A1 | 11/2017 | Fosdick |
| 2018/0279643 A1 | 10/2018 | Barkalow et al. |
| 2020/0054049 A1 | 2/2020 | Kim et al. |

FOREIGN PATENT DOCUMENTS

| | | |
|---|---|---|
| KR | 20160098249 | 8/2016 |
| KR | 20190000357 | 1/2019 |
| WO | 2015075473 A1 | 5/2015 |
| WO | 2015094342 A1 | 6/2015 |
| WO | 2018084535 A1 | 5/2018 |

BINDING SYRUP COMPOSITION COMPRISING ALLULOSE AND LOW SUGAR SYRUPS, PRODUCTS CONTAINING THE SYRUP COMPOSITION AND METHODS OF MAKING

This application claims priority to U.S. Provisional Patent Application Nos. 62/844,829, filed May 8, 2019 and 62/895,253, filed Sep. 3, 2019, which are both incorporated herein by reference in their entireties.

The invention relates to binding syrup compositions for formulating food products containing allulose and low sugar syrups having low mono- and di-saccharide content. The binding syrup compositions allow food products with reduced caloric and sugar content to be produced while overcoming formulation limitations of allulose-containing products, including product stickiness and failure to maintain product shape and texture in comparison to full sugar equivalents. Various food product compositions containing the binding syrup composition and methods of making the same are also provided.

Sweeteners and sugars are commonly included in food products. Nutritive sweeteners include sucrose (i.e. table sugar), glucose, fructose, corn syrup (including high fructose corn syrup), maltose, lactose, molasses, honey, agave and others. Natural and synthetic sweeteners (i.e. artificial sweeteners) are an alternative to nutritive sweeteners as they provide desirable taste characteristics as well as other functional properties with significantly lower caloric content. Such sweeteners can include high potency or high intensity sweeteners (e.g. Splenda), sugar alcohols or polyols (e.g. xylitol, sorbitol, etc.), stevia sweeteners, rare sugars, and the like.

Allulose (also referred to as D-allulose, psicose, D-psicose) is a non-nutritive sweetener that is found naturally in certain foods and has been formulated into various food and beverage products. Allulose is considered a 'rare sugar' as it is found in nature in very small amounts. Allulose provides approximately 70% of the sweetness of sucrose with only 5% of the calories (approximately 0.2 kcal/g) and is often considered to be a 'zero calorie' sweetener.

There is an ongoing preference in various food products to reduce consumer intake of nutritive sweeteners, in order to provide both caloric reduction and total sugar reduction. Accordingly, there has been an increase in the use of natural and synthetic sweeteners in food product compositions. U.S. Publication No. 2016/0331014 provides a solid food product with D-allulose syrup containing fructose and other sugars with the D-allulose to provide product hardness resulting from quick-hydration of the drug ingredients along with aiding in improved cohesiveness of a dough bar to reduce stickiness and improve the manufacturing processing. However, the products were not reproducible and are contradictory to formulations according to the invention which exhibit significant decreases in hardness of bar food products as allulose levels increase.

Other food products containing high levels of allulose have been made in an attempt to provide food products exhibiting the desired bulking, sweetening and functional properties traditionally provided by nutritive sweeteners. See WO2015/075473. However, such formulations fail to adjust the formulation to overcome the high hygroscopicity contributed by the monosaccharides contained in the allulose, and therefore do not provide reduced sugar food products exhibiting the properties desired by consumers and food manufacturers.

Accordingly, disclosed herein are food composition products formulated with a binding bar syrup composition containing allulose and low sugar syrups having reduced sugar content and reduced calories. Further disclosed herein are food composition products, such as bars, having hardness and texture profiles equivalent to full sugar controls that do not benefit from the use of the binding bar syrup composition to reduce sugar and calories.

Disclosed herein are binding bar syrup compositions, food product compositions incorporating the binding bar syrup compositions, and methods of making the same, wherein such compositions are able to use allulose to reduce sugar and calories in food products while maintaining hardness and texture profiles that are equivalent to those of full sugar products.

In one embodiment, binding bar syrup compositions comprise allulose; and at least one low sugar syrup and optionally additional syrup, wherein the binding bar syrup composition has a DP1+DP2 content less than about 65%, and/or a DP3+ content of greater than about 35%. In another embodiment, the low sugar syrup has a total DP1 and DP2 content of less than 25%, or less than about 20%. In some embodiments the allulose is a liquid syrup comprising at least about 85% purity, at least about 90% purity, or at least about 95% purity and at least about 65% by weight solids. In some embodiments, the allulose is a liquid syrup comprising at least about 85% allulose, 90% allulose, or 95% allulose and the remainder of the syrup comprising other monosaccharides and/or disaccharides. In some embodiments, the low sugar syrup has a total DP1 and DP2 content of less than about 25%, less than about 20%, less than about 19%, less than about 18%, less than about 17% less than about 16%, less than about 15%, less than about 14%, less than about 13%, less than about 12%, less than about 11%, or less than about 10%. In some embodiments, the composition does not include sucrose or any nutritive sweetener. In some embodiments, the composition further comprises at least one additional binder ingredient, including at least one of water, glycerin, nut butter, flavorings and/or extracts, flavoring liquor, such as chocolate liquor, salt, oil, and maltodextrin, and comprises up to about 50 wt-% of the composition, or from about 12.5 wt-% and about 50 wt-%. In some embodiments, the allulose comprises between about 7.5 wt-% and about 50 wt-% of the composition and the low sugar syrup comprises between about 12.5 wt-% and about 75 wt-% of the composition.

In an additional embodiment, food product compositions comprising the binding bar syrup compositions and dry ingredients are provided. The dry ingredients in the food product can include, for example, one or more of oat, rice, barley, dried fruit, nuts, protein isolate, and cocoa powder. The binding bar syrup composition can further include additional binder ingredients, including for example, at least one of water, glycerin, nut butter, flavorings and/or extracts, flavoring liquor, salt, oil, and maltodextrin. In some embodiments, the food product composition is free of at least one of water, glycerin, and sucrose. In an embodiment, the food product composition comprises the binding bar syrup between about 35 wt-% to about 65 wt-% of the composition and the dry ingredients between about 35 wt-% to about 65 wt-% of the composition. In still other embodiments, the food product composition is a bar, including for example, a granola bar, snack bar, high protein bar, high fiber bar, sports nutrition bar, energy bar, recovery bar, confectionery bar, or breakfast bar. Beneficially, the food product composition has a 2 week measured hardness (grams force) that is at least equivalent or greater than a full sugar control formulation, or at least about 6,000 g force at 2 weeks.

In an additional embodiment, methods of making a food product composition are provided and include combining the binding bar syrup composition with dry ingredients; blending to form a substantially homogenous food product composition; and molding to form a food product composition in the form of a bar. In an embodiment, the binding bar syrup is initially cooked to at least about 75° Brix, 76° Brix, 77° Brix, 78° Brix, 79° Brix, 80° Brix, 81° Brix, 82° Brix, 83° Brix, or 84° Brix before combining with the dry ingredients. In an embodiment, the methods also include cutting the molded bar food product composition. In yet other embodiments, the bar is a granola bar, snack bar, high protein bar, high fiber bar, sports nutrition bar, energy bar, recovery bar, confectionery bar, or breakfast bar. In other embodiments, the bar composition employing the binding bar syrup composition reduces the calories of the bar by at least about 10%, at least about 12%, or at least about 15%. In still other embodiments, the bar composition employing the binding bar syrup composition reduces the sugar content of the bar by at least about 20%, at least about 25%, or at least about 30%.

Various embodiments of the present invention will be described in detail with reference to the drawings, wherein like reference numerals represent like parts throughout the several views. And while multiple embodiments are disclosed herein, still other embodiments will become apparent to those skilled in the art from the following detailed description, which shows and describes illustrative embodiments. As a result, reference to various embodiments does not limit the scope of the invention. Additionally, the figures represented herein are not limitations to the various embodiments according to the invention and are presented for exemplary illustration of the invention. Accordingly, the drawings and detailed description are to be regarded as illustrative in nature and not restrictive.

All terminology used herein is for the purpose of describing particular embodiments only, and is not intended to be limiting in any manner or scope. For example, as used in this specification and the appended claims, the singular forms "a," "an" and "the" can include plurals unless the context clearly indicates otherwise. Further, all units, prefixes, and symbols may be denoted in its SI accepted form. Numeric ranges recited within the specification are inclusive of the numbers within the defined range. Throughout this disclosure, various aspects are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments without undue experimentation. In describing and claiming the embodiments, the following terminology will be used in accordance with the definitions set out below.

The term "about," as used herein, refers to variations in the numerical quantity that can occur, for example, through typical measuring and handling procedures; through inadvertent error in these procedures; through differences in the manufacture, source, or purity of the ingredients; and the like. Whether or not modified by the term "about", the claims include equivalents to the quantities.

As used herein, the term "DE" or "Dextrose Equivalent" refers to the degree of starch hydrolysis, specifically reducing the value of a starch hydrolysate compared to the reducing value of an equal weight of dextrose, expressed as percent, dry basis, as measured by the Lane any Eynon method described in Standard Analytical Method E-26, Corn Refiners Association, 6$^{th}$ Edition 1977, pp. 1-3.

As used herein, the term "DP" refers to the number of saccharide units. For example "DP1" saccharide is intended herein to refer to a monosaccharide, such as dextrose.

As used herein, the term "free" refers to compositions completely lacking the component or having such a small amount of the component that the component does not affect the performance of the composition. The component may be present as an impurity or as a contaminant and shall be less than 0.5 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions may comprise, consist essentially of, or consist of the components and ingredients as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Binding Bar Syrup Compositions

The binding bar syrup compositions include allulose and low sugar syrups having low mono- and di-saccharide content. The binding bar syrup composition reduces the DP1+DP2 content of the low sugar syrups combined with allulose to reduce caloric and/or sugar content while maintaining desired attributes, e.g. texture, hardness, stickiness and shape, and binding capabilities of a full-sugar bar food product while also enabling corn syrup to be removed from the syrup and food products. In another embodiment, the increased DP3+ content (trisaccharide and larger saccharides) of the binding bar syrup increases the stability of the food composition containing the binding bar syrup over the shelf-life of the composition. In further embodiments of the binding bar syrup compositions and food product compositions containing such syrups, corn syrups are replaced with allulose and the formulations are further modified by combining low sugar syrups with allulose to achieve the improved low calorie and low sugar food compositions described herein.

In exemplary embodiments, the binding bar syrup compositions have a DP1+DP2 content less than about 65%, and/or a DP3+ content of greater than about 35%. In other embodiments, the binding bar syrup composition has a ratio of the DP3+ to DP1 content greater than about 0.5. In even further embodiments, the binding bar syrup composition has a ratio of the DP1 to DP3+ content less than about 2.0. In additional embodiments, the binding bar syrup contains a ratio of the allulose to the low sugar syrup from about 25:75 to about 75:25. Exemplary binding bar syrup compositions are shown in Table A in weight percentage (dry basis).

TABLE A

| Material | First Exemplary Range wt-% | Second Exemplary Range wt-% | Third Exemplary Range wt-% |
|---|---|---|---|
| Allulose | 7.5-50 | 15-50 | 15-37.5 |
| Low Sugar Syrups | 12.5-75 | 12.5-50 | 15-45 |
| Additional Binder Ingredients | 0-50 | 12.5-50 | 20-45 |

Allulose

The binding bar syrup compositions include an allulose source. Allulose is a commercially-available monosaccharide having the following structure, which is a C3 epimer of D-fructose:

Allulose is available in crystalline form or in the form of a syrup comprising allulose. The syrup forms comprise allulose in varying amounts of percent solids (generally between about 60% to about 90% by weight).

An exemplary allulose source is available under the tradename ASTRAEA® Liquid Allulose, with 95% purity (dry solids basis, ds or DS) and at 74% solids. Additional allulose sources may have a purity (expressed as weight % allulose, based on the total weight of the allulose source) of at least 80%, at least 85%, at least 90%, at least 95%, at least 96%, at least 97%, at least 98%, at least 99%, or at least 99.9%, or 100% pure allulose. Additional allulose sources may have a percent solids of at least about 65%, at least about 70%, at least about 75%, or greater.

In some embodiments, the allulose source is a mixture of allulose and additional monosaccharides and disaccharides, determined according to the purity level of the allulose. In some embodiments, the allulose source may be an admixture of allulose and one or more other sugars, such as fructose. In some embodiments the allulose source is a syrup comprising from about 85 wt-% to about 95 wt-% allulose and from about 5 wt-% to about 15 wt-% of monosaccharides and disaccharides, based on the dry matter content of the syrup.

In one embodiment, the allulose comprises from about 7.5 wt-% to about 50 wt-% of the binder bar syrup composition, from about 15 wt-% to about 50 wt-% of the binding bar syrup composition, from about 15 wt-% to about 37.5 wt-% of the binding bar syrup composition, or from about 15 wt-% to about 30 wt-% of the binding bar syrup composition.

In a further embodiment, the allulose comprises from about 5 wt-% to about 20 wt-% of the food product composition, from about 10 wt-% to about 20 wt-% of the food product composition, from about 10 wt-% to about 15 wt-% of the food product composition, or from about 10 wt-% to about 12 wt-% of the food product composition.

Low Sugar Syrups

The binding bar syrup compositions include at least one low sugar syrup having low mono- and di-saccharide content. In some embodiments, the binding bar syrup compositions include a combination of at least two low sugar syrups having low mono- and di-saccharide content. Low mono- and di-saccharide content (DP1 and DP2, respectively) as referred to herein means at least about 50%, 55%, 60%, 70%, or less DP1 and DP2 compared to full sugar syrup (i.e. standard glucose, corn syrup or tapioca syrup). In an exemplary embodiment, a DP1 and DP2 content of a low sugar syrup has at least 50% less DP1 and DP2 content compared to a full sugar syrup.

In another embodiment the low sugar syrup(s) have a DP1 and DP2 content of less than about 25%, less than about 20%, less than about 18%, less than about 17%, or less than about 16%.

Exemplary low sugar syrups are available under the tradenames VERSASWEET® 1524 glucose syrup, VERSASWEET® 1526 glucose syrup, VERSASWEET® 1526 NGM glucose syrup, VERSASWEET® 1531 glucose syrup, STABLESWEET® glucose syrup, BIOLIGIO® ML6810 glucose syrup, MULTIVANTAGE® syrup, VERSYRA™ corn syrup, and CLEARDEX® glucose syrup.

In other embodiments the low sugar syrup is combined with additional sugar syrup to assist in decreasing the overall combined mono- and di-saccharide content (DP1 and DP2, respectively) of the binding bar syrup composition. For example, in certain embodiments, such as cereal bars (e.g. non-protein bars), the combination of allulose, low sugar syrup, and optional additional sugar syrup, the DP1 and DP2 content are between about 8% and about 15%, about 8% and about 13%, or between about 8% and about 12%. In still other embodiments, such as protein bars, the combined mono- and di-saccharide content (DP1 and DP2, respectively) of the allulose, low sugar syrup, and optional additional sugar syrup of the binding bar syrup composition is less than about 65%, less than about 60%, less than about 55%, less than about 50%, less than about 45%, less than about 40%, less than about 35%, less than about 30%, or less than about 25%.

Beneficially and without limiting any particular mechanism of action or theory of the invention, the combination of low sugar syrup with the allulose in the binding bar syrup overcomes the high monosaccharide (DP1) content and hygroscopicity of the allulose to provide desirable textural attributes and binding characteristics for the food product compositions in which the binding bar syrup is formulated.

In one embodiment, the low sugar syrup(s) comprise from about 12.5 wt-% to about 75 wt-% of the binding bar syrup composition, from about 12.5 wt-% to about 50 wt-% of the binding bar syrup composition, from about 15 wt-% to about 45 wt-% of the binding bar syrup composition.

In a further embodiment, the low sugar syrup(s) comprise from about 5 wt-% to about 30 wt-% of the food product composition, from about 5 wt-% to about 20 wt-% of the food product composition, from about 8 wt-% to about 18 wt-% of the food product composition, from about 10 wt-% to about 15 wt-% of the food product composition.

In yet another embodiment, the low sugar syrup(s) replace or substantially reduce the use of nutritive sweeteners, such as sucrose, glucose, fructose, corn syrup, high fructose corn syrup, etc. in the binding syrup, such that the nutritive sweeteners contained in the binding bar syrup compositions described herein can be reduced by at least about 10%, 20%, 30%, 40%, 50%, 60%, 70%, 80%, 90% or 100%.

Additional Binder Ingredients

The binding bar syrup compositions may optionally include additional binder ingredients. The presence of additional binder ingredients will vary based upon the particular food product formulated with the binder bar syrup composition. Exemplary additional binder ingredients include, for example, water, glycerin, nut butters, flavorings and/or extracts (e.g. vanilla, maple, malt extract) and/or flavoring liquor (e.g. chocolate liquor which is a chocolate mass containing equal parts cocoa solids and cocoa butter), salt, fats and oils (e.g. canola oil), bulking agents including starches (e.g. maltodextrin, polydextrose, xanthan gum, guar gum, soluble corn fiber, and the like), polyols (e.g. sorbitol, maltitol, erythritol and the like) and additional or co-sweeteners (e.g. corn/glucose syrup solids). Any combinations of the additional binder ingredients can be incorporated into the binding bar syrup compositions.

In some embodiments, the binding bar syrup composition is free of at least one of water, glycerin, and sucrose. In other embodiments, the binding bar syrup composition includes a maltodextrin with a reduced DE with lower DP1+DP2 to further reduce the DP1+DP2 content. In one embodiment, the maltodextrin has a DE equal to or less than 18, or equal to or less than 10. In other embodiments, the binding bar syrup composition is free of maltodextrin and replaced with a low sugar syrup.

In still another embodiment, additional binder ingredients comprise from about 0 wt-% to about 50 wt-% of the binding bar syrup composition, from about 12.5 wt-% to about 50 wt-% of the binding bar syrup composition, or from about 20 wt-% to about 45 wt-% of the binding bar syrup composition.

In yet a further embodiment, the additional binder ingredients comprise from about 0 wt-% to about 25 wt-% of the food product composition, from about 5 wt-% to about 20 wt-% of the food product composition, from about 10 wt-% to about 20 wt-% of the food product composition, or from about 10 wt-% to about 15 wt-% of the food product composition.

Food Products Containing the Binding Bar Syrup Compositions

Various food products can be produced using the binding bar syrup compositions comprising allulose and low sugar syrups, including for example baked goods and bars. In an embodiment, the food product composition is a bar. Exemplary bars include, for example, granola bar, snack bar, high protein bar, high fiber bar, sports nutrition bars, energy bars, recovery bars, confectionery bars, breakfast bars, and the like. Bars can include cereal, nut, seed, protein and/or fruit bars.

In an embodiment, the food product composition comprises the binding bar syrup composition and dry ingredients. Exemplary dry ingredients include, for example, cereals, oats, rice, barley, dried fruit, nuts, protein isolate, spices, vegetable and vegetable-derived products, legumes and legume-derived products, starch-based ingredients, proteins, cocoa powder, chocolate chips, dietary fibers, protein crisps, and the like. In an embodiment, the dry ingredients comprise from about 50 wt-% to about 70 wt-% of the food product composition, from about 55 wt-% to about 70 wt-% of the food product composition, from about 55 wt-% to about 60 wt-% of the food product composition, or about 60 wt-% of the food product composition.

Exemplary food product compositions are shown in Tables B and C in weight percentage (dry basis).

TABLE B

| Material | First Exemplary Range wt.-% | Second Exemplary Range wt.-% | Third Exemplary Range wt.-% |
| --- | --- | --- | --- |
| Allulose | 5-20 | 10-20 | 10-15 |
| Low Sugar Syrups | 5-20 | 8-18 | 10-15 |
| Additional Binder Ingredients | 0-50 | 5-45 | 10-45 |
| Dry Ingredients | 25-70 | 30-70 | 30-65 |

TABLE C

| Material | First Exemplary Range wt.-% | Second Exemplary Range wt.-% | Third Exemplary Range wt.-% |
| --- | --- | --- | --- |
| Binding Bar Syrup Composition | 30-75 | 30-70 | 35-70 |
| Dry Ingredients | 25-70 | 30-70 | 30-65 |

In one embodiment, the binding bar syrup composition comprises about 40 wt-% of the food product composition and the dry ingredients comprise about 60 wt-% of the food product composition.

In another embodiment, the food product composition containing the binding bar syrup composition achieves at least about a 10%, at least about a 12%, or at least about a 15% reduction in calories compared to a control food product containing corn syrup (e.g. 42DE corn syrup) instead of the binding bar syrup composition described herein. In a further embodiment, the food product composition containing the binding bar syrup composition achieves at least about a 20%, at least about a 25%, or at least about a 30% reduction in sugar compared to a control food product containing corn syrup instead of the binding bar syrup composition described herein.

In an embodiment, the food product composition containing the binder bar syrup composition described herein has an equivalent hardness compared to a full sugar control food product composition that does not contain the binder bar syrup composition (both measured according to grams force as a hardness value and based on sensory evaluations). As referred to herein, a "full sugar" or "full sugar control" product refers to a composition that does not contain a binding bar syrup composition described herein and instead contains a full sugar equivalent composition that is substantially made of (at least about 95% of the sugar source) 40-43 DE corn syrup and/or 60-63 DE corn syrup. In yet another embodiment, the hardness at 2 weeks of a bar food product containing the binding bar syrup composition described herein is at least equivalent to or greater than a bar food product containing a corn syrup control (as referred to herein as a full sugar control) composition measured by average hardness (grams force) as set forth in the Examples. In another embodiment, the 2 week hardness of a chewy bar formulation containing the binding bar syrup composition described herein is at least about 6,000 grams force. The grams of force is a peak force measurement of the maximum force that occurs during the first compression of the bar.

Methods of Making

The method of making a food product composition comprising the binding bar syrup composition includes the steps of combining the binding bar syrup composition at a point of use, such that the allulose and low sugar syrup are combined to form the binding bar syrup composition and then also combined with the dry ingredients.

The binding bar syrup composition is heated to a desired Brix measurement (measurement of sugar content in aqueous solution where one degree Brix is 1 gram of sucrose in 100 grams of solution). In an embodiment, the binding bar syrup composition is heated to a Brix measurement of at least about 75° Brix, 76° Brix, 77° Brix, 78° Brix, 79° Brix, 80° Brix, 81° Brix, 82° Brix, 83° Brix, or 84° Brix, or other desired Brix measurement. In another embodiment, the allulose is added to the low sugar syrup and any additional syrups and/or additional binding agents that comprise the binding bar syrup composition and heated up to the target Brix. The heated binding bar syrup composition is then combined with the dry ingredients.

In an embodiment, the binding bar syrup composition comprises between about 35 wt-% to about 65 wt-% of the food product composition and the dry ingredients comprise between about 35 wt-% to about 65 wt-% of the food product composition. In one embodiment, the binding bar syrup composition comprises between about 35 wt-% to about 45 wt-% of a chewy food product composition and the dry ingredients comprise between about 55 wt-% to about 65 wt-% of the chewy food product composition. In another embodiment, the binding bar syrup composition comprises about 40 wt-% of the chewy food product composition and the dry ingredients comprise about 60 wt-% of the chewy food product composition. In yet another embodiment, the binding bar syrup composition comprises between about 60 wt-% to about 65 wt-% of a high protein food product composition and the dry ingredients comprise between about 35 wt-% to about 40 wt-% of the high protein food product composition. In a still further embodiment, the binding bar syrup composition comprises about 63 wt-% of the high protein food product composition and the dry ingredients comprise about 37 wt-% of the high protein food product composition. The combining of the binding bar syrup composition and dry ingredients are then blended to form a substantially homogenous food product composition.

The methods can further include steps of molding the food product composition and cutting the food product composition into desired shapes and sizes.

Beneficially, the use of the binding bar syrup composition reduces the calories of the bar by at least about 10%, at least about 12%, or at least about 15% compared to a bar made with corn syrup. As a still further benefit, the use of the binding bar syrup composition reduces the sugar content of the bar by at least about 20%, at least about 25%, or at least about 30% compared to a bar made with corn syrup. Both the caloric reduction and sugar content reduction are achieved while maintaining a substantially similar hardness (both measured according to grams force as a hardness value and based on sensory evaluations) of the food product compared to a control made with corn syrup.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Making and Analyzing Chewy Granola Bars Containing a Binding Bar Syrup Composition Chewy granola bars were prepared by cooking respective binding bar syrup compositions to 82.5° Brix and combining with the dry ingredients. The bars were molded and cut into 3×10 cm pieces.

Hardness was measured at 2 week time mark, which is considered the time frame for the bars to fully set. Bar hardness was assessed using texture analysis (Stable Micro Systems TAXT2 Texture Analyzer) bar cut test as follows:
1) Use 30 kg or 50 kg load cell;
2) Attach TA 45° chisel blade;
3) Adjust analyzer settings as follows:
   (i) Option: Return to start (Special Tests);
   (ii) Test Mode: Compression;
   (iii) Pre-test speed: 2 mm/s;
   (iv) Test speed: 3 mm/s;
   (v) Post-test speed: 10 mm/s;
   (vi) Target Mode: Distance, 14 mm;
   (vii) Trigger Type: Auto;
   (viii) Trigger Force: 15 g; and
   (ix) Data acquisition points: 200 pps.

Center bar under blade so that the long edge of the bar is perpendicular to the blade edge. Record Firmness (Peak Force (g)). Perform 3 readings per sample from 5 individual bars, totaling 15 readings.

The water activity of the bars was also measured as follows (using Rotronic HygroLab3):
1) Load analysis cup to halfway line with crumbled bar pieces; and
2) Record average of 4 replicates.

The allulose used in this study is a Liquid Allulose, with 95% purity and at 74% solids. Table 1 shows a Control chewy granola bar formulation where the main binder syrup component is the 42 DE corn syrup as Example 1A. Table 1 also shows chewy granola bar formulations containing allulose at 5% and 10% (dry basis) to replace a portion of the 42 DE corn syrup as Examples 1B and 1D.

TABLE 1

Chewy Granola Bar Formulas Containing 5% and 10% Allulose

| | Ingredients | 42 DE Corn Syrup Control Ex. 1A % | 5% Allulose + 42 DE Corn Syrup Ex. 1B % | 5% Allulose + LSS Ex. 1C % | 10% Allulose + 42 DE Corn Syrup Ex. 1D % | 10% Allulose + LSS Ex. 1E % | 10% Allulose + LSS (no sucrose) Ex. 1F % |
|---|---|---|---|---|---|---|---|
| Dry Ingredients | Toasted oats | 20.36 | 20.36 | 20.36 | 20.36 | 20.36 | 20.36 |
| | Crisp rice | 16.23 | 16.23 | 16.23 | 16.23 | 16.23 | 16.23 |
| | Barley flakes | 13.66 | 13.66 | 13.66 | 13.66 | 13.66 | 13.66 |
| | Dried Cranberries | 9.75 | 9.75 | 9.75 | 9.75 | 9.75 | 9.75 |

TABLE 1-continued

Chewy Granola Bar Formulas Containing 5% and 10% Allulose

| Ingredients | | 42 DE Corn Syrup Control Ex. 1A % | 5% Allulose + 42 DE Corn Syrup Ex. 1B % | 5% Allulose + LSS Ex. 1C % | 10% Allulose + 42 DE Corn Syrup Ex. 1D % | 10% Allulose + LSS Ex. 1E % | 10% Allulose + LSS (no sucrose) Ex. 1F % |
|---|---|---|---|---|---|---|---|
| Binder Ingredients | 42 DE Corn Syrup | 21.99 | 15.78 | — | 9.58 | — | — |
| | Liquid Allulose | — | 6.76 | 6.76 | 13.51 | 13.51 | 13.51 |
| | Low Sugar Syrup (LSS) | — | — | 16.10 | — | 9.77 | 11.79 |
| | Water | 1.98 | 1.43 | 1.11 | 0.87 | 0.68 | 0.26 |
| | Sugar, extra fine | 1.59 | 1.59 | 1.59 | 1.59 | 1.59 | — |
| | Malt extract | 2.29 | 2.29 | 2.29 | 2.29 | 2.29 | 2.29 |
| | Glycerin | 2.32 | 2.32 | 2.32 | 2.32 | 2.32 | 2.32 |
| | Salt | 0.25 | 0.25 | 0.25 | 0.25 | 0.25 | 0.25 |
| | Canola Oil | 3.07 | 3.07 | 3.07 | 3.07 | 3.07 | 3.07 |
| | Maltodextrin, 18 DE | 6.18 | 6.18 | 6.18 | 6.18 | 6.18 | 6.18 |
| Flavoring | Vanilla extract | 0.17 | 0.17 | 0.17 | 0.17 | 0.17 | 0.17 |
| | Maple flavor | 0.17 | 0.17 | 0.17 | 0.17 | 0.17 | 0.17 |
| Totals | | 100 | 100 | 100 | 100 | 100 | 100 |

It was observed that when standard 42DE corn syrup was replaced with allulose, the binding properties and the texture of the formed bars were notably different than those of control (see data in Table 2). As allulose content increased, the binding properties worsened, and the resulting hardness in the bars decreased, making the bars less stable in shape.

Additional chewy granola bar formulations were made by adding low sugar syrup, which is a low sugar syrup with mono- and di-saccharide content of less than 16%, to chewy granola bar formulations containing allulose at 5% and 10% (dry basis), which are set forth in Table 1 as Examples 1C and 1E. The low sugar syrup replaced the 42 DE corn syrup that remained in the 5% and 10% allulose formulations of Examples 1B and 1D shown in Table 1. One additional chewy granola bar formulation shown as Example 1F in Table 1 was prepared where the sucrose in the binder syrup was also replaced with the low sugar syrup in the 10% allulose containing chewy granola bar formulation set forth as Example 1D in Table 1. In all formulations, the syrup and water levels were adjusted to keep the initial dry solids content of the binding syrups constant.

The DP distribution of the 42 DE corn syrup, low sugar syrup, and liquid allulose is shown in Table 2. As mentioned, the addition of allulose increased the DP1 content of the syrup and reduced the viscosity of the syrup, resulting in the bars being more crumbly and softer in texture from a decrease in binding properties which is undesirable. The low sugar syrup contains half the amount of DP1 and DP2 content (about 16%) versus 42 DE corn syrup (about 34%). So, replacing 42 DE corn syrup with low sugar syrup reduces the DP1 and DP2 content in the binding syrup, improving the binding properties of the bar binding syrup and the resulting textural attributes in the finished bar.

TABLE 2

DP Distribution For 42 DE Corn Syrup, Low Sugar Syrup and Liquid Allulose (dry basis)

| | DP Distribution (% area) | | |
|---|---|---|---|
| Ingredient | DP1 | DP2 | DP3+ |
| 42 DE Corn Syrup | 20.2 | 13.9 | 65.9 |
| Low Sugar Syrup | 4.9 | 11.0 | 84.1 |
| Liquid Allulose | 99.8 | 0.1 | 0.1 |

Tables 3A-3B show the evaluated binding syrups, including full sugar binding syrups and evaluated binding bar syrups DP1, DP2 and DP3+ contents in percentages.

Table 3A shows the DP1, DP2 and DP3+ content of the chewy granola bar binding syrup compositions. Replacing the standard 42 DE corn syrup with low sugar syrup brings the DP1 and DP2 content closer to the Example 1A Control bar, which improves binding and textural attributes. Removing sucrose from the formula further reduced DP2 content. The low sugar syrups allow for additional sugar reduction versus using standard 42 DE corn syrup (as in the Example 1A Control).

TABLE 3A

DP1, DP2 & DP3+ Content of the Chewy Granola Bar Binding Syrups including allulose) Used in Examples 1A-1F

| Bar Binding Syrup | DP1 (% db) | DP2 (% db) | DP1 + DP2 (% db) | DP3+ (% db) |
|---|---|---|---|---|
| Example 1A | 4.68 | 4.40 | 9.08 | 17.82 |
| Example 1B | 8.67 | 3.71 | 12.38 | 14.52 |
| Example 1C | 6.72 | 3.33 | 10.05 | 16.95 |
| Example 1D | 12.65 | 3.01 | 15.66 | 11.22 |

TABLE 3A-continued

DP1, DP2 & DP3+ Content of the Chewy Granola Bar
Binding Syrups including allulose) Used in Examples 1A-1F

| Bar Binding Syrup | DP1 (% db) | DP2 (% db) | DP1 + DP2 (% db) | DP3+ (% db) |
|---|---|---|---|---|
| Example 1E | 11.48 | 2.79 | 14.27 | 12.70 |
| Example 1F | 11.55 | 1.37 | 12.92 | 14.05 |

TABLE 3B

Converted the DP content to percentage in binding syrup

| Bar Binding Syrup | DP1 (%) | DP2 (%) | DP1 + DP2 (%) | DP3+ (%) |
|---|---|---|---|---|
| Example 1A | 17.40 | 16.35 | 33.75 | 66.25 |
| Example 1B | 32.23 | 13.79 | 46.02 | 53.98 |
| Example 1C | 24.89 | 12.33 | 37.22 | 62.78 |
| Example 1D | 47.06 | 11.20 | 58.26 | 41.74 |
| Example 1E | 42.57 | 10.34 | 52.91 | 47.09 |
| Example 1F | 42.83 | 5.08 | 47.91 | 52.09 |

Table 4 shows hardness results for chewy granola bar formulations prepared with 5% and 10% allulose. As mentioned before, bar hardness decreased as the allulose level increased up to 10% (From 1A to 1B to 1D). For chewy granola bar formulations containing 5% and 10% allulose, the combination of allulose and LSS resulted in moving the hardness values towards Control versus allulose in combination with standard 42 DE corn syrup (1C vs 1B and 1E vs 1D); removing sucrose and replacing it with LSS also helped to increase hardness making the 10% Allulose containing bars very comparable to the Control bars (1F very comparable to 1A).

TABLE 4

Hardness Results for Chewy Granola Bars Containing
5% and 10% Allulose after 2 weeks

| Chewy Granola Bar Formulations | Average Hardness (g force) 2 weeks |
|---|---|
| Example 1A | 6,219 ± 706 |
| Example 1B | 5,204 ± 766 |
| Example 1D | 3,851 ± 605 |
| Example 1C | 5,837 ± 696 |
| Example 1E | 4,351 ± 534 |
| Example 1F | 6,351 ± 948 |

Additional chewy granola bars were formulated with increased allulose content. Table 5 shows the chewy granola bar formulations with 12% and 15% allulose (dry basis) as Example 1G-1L. It was not possible to prepare bars with just 12% and 15% allulose incorporation (the remaining of the main binder syrup being standard 42DE corn syrup) as the resulting binder syrup was not able to bind the granola and other larger ingredients satisfactorily. Formulations were then made where LSS was utilized along with various other formulation changes to improve the binding properties and textural attributes. These formulation changes included removal of water, removal of sucrose, reduction and/or removal of glycerin, and changing from 18DE Maltodextrin (MDX) to 10DE Maltodextrin.

TABLE 5

Chewy Granola Bar Formulas Containing 12% and 15% Allulose

| | Ingredients | 12% Allulose + LSS (50% glycerin) 1G % | 12% Allulose + LSS (no glycerin) 1H % | 12% Allulose + LSS (50% glycerin, 10 DE MDX) 1I % | 12% Allulose + LSS (no glycerin, no MDX) 1J % | 15% Allulose + LSS (no glycerin, 10 DE MDX) 1K % | 15% Allulose + LSS (no glycerin, no MDX) 1L % |
|---|---|---|---|---|---|---|---|
| Dry Ingredients | Toasted oats | 20.36 | 20.36 | 20.36 | 20.36 | 20.36 | 20.36 |
| | Crisp rice | 16.23 | 16.23 | 16.23 | 16.23 | 16.23 | 16.23 |
| | Barley flakes | 13.66 | 13.66 | 13.66 | 13.66 | 13.66 | 13.66 |
| | Dried Cranberries | 9.75 | 9.75 | 9.75 | 9.75 | 9.75 | 9.75 |
| Binder Ingredients | LSS | 10.50 | 11.66 | 10.50 | 16.67 | 7.60 | 13.78 |
| | Liquid Allulose | 16.22 | 16.22 | 16.22 | 16.22 | 20.27 | 20.27 |
| | Malt extract | 2.29 | 2.29 | 2.29 | 2.29 | 2.29 | 2.29 |
| | Glycerin | 1.16 | — | 1.16 | 1.16 | — | — |
| | Salt | 0.25 | 0.25 | 0.25 | 0.25 | 0.25 | 0.25 |
| | Canola Oil | 3.07 | 3.07 | 3.07 | 3.07 | 3.07 | 3.07 |
| | Maltodextrin, 18DE | 6.18 | 6.18 | — | — | — | — |
| | Maltodextrin, 10DE | — | — | 6.18 | — | 6.18 | — |
| Flavoring | Vanilla extract | 0.17 | 0.17 | 0.17 | 0.17 | 0.17 | 0.17 |
| | Maple flavor | 0.17 | 0.17 | 0.17 | 0.17 | 0.17 | 0.17 |
| Totals | | 100 | 100 | 100 | 100 | 100 | 100 |

Tables 6A-6B show the DP1, DP2 and DP3+ content for the 12% and 15% allulose bars according to Table 5.

TABLE 6A

DP1, DP2 & DP3+ Content of the Chewy Granola Bar Binding Syrups

| Bar Binding Syrup | DP1 (% db) | DP2 (% db) | DP1 + DP2 (% db) | DP3+ (% db) |
|---|---|---|---|---|
| Example 1G | 13.51 | 1.27 | 14.78 | 13.24 |
| Example 1H | 13.56 | 1.38 | 14.94 | 14.03 |
| Example 1I | 13.45 | 1.04 | 14.49 | 13.53 |
| Example 1J | 13.63 | 1.47 | 15.10 | 12.09 |
| Example 1K | 16.34 | 0.79 | 17.13 | 11.58 |
| Example 1L | 16.52 | 1.21 | 17.73 | 10.12 |

TABLE 6B

Converted the DP Content to Percentage in Binding Syrup

| Bar Binding Syrup | DP1 (%) | DP2 (%) | DP1 + DP2 (%) | DP3+ (%) |
|---|---|---|---|---|
| Example 1G | 48.22 | 4.53 | 52.75 | 47.25 |
| Example 1H | 46.81 | 4.76 | 51.57 | 48.43 |

TABLE 6B

Converted the DP Content to Percentage in Binding Syrup

| Bar Binding Syrup | DP1 (%) | DP2 (%) | DP1 + DP2 (%) | DP3+ (%) |
|---|---|---|---|---|
| Example 1I | 48.00 | 3.71 | 51.71 | 48.29 |
| Example 1J | 50.13 | 5.41 | 55.54 | 44.46 |
| Example 1K | 56.91 | 2.75 | 56.97 | 40.33 |
| Example 1L | 59.32 | 4.34 | 63.66 | 36.34 |

Table 7 shows hardness results for chewy granola bars prepared with 12% and 15% Allulose. As mentioned before, just replacing Allulose at these levels with standard 42DE syrup resulted in poor binding properties and did not allow for any successful bar formation. And as the allulose level increased, the extent of the problem increased as well. Therefore, in addition to formulating with the low sugar syrup (LSS), other formulation adjustments were implemented to bring the texture closer to the Control. Acceptable bars with higher allulose inclusion levels could be made through removal of sucrose, reduction/removal of glycerin, changing from 18 DE Maltodextrin to 10 DE Maltodextrin, and replacing maltodextrin with LSS. At 12% Allulose level, the closest bar hardness to Control was achieved when LSS was used and glycerin was eliminated. At 15% Allulose level, the closest bar hardness was achieved when LSS was used, and a lower DE maltodextrin was utilized.

TABLE 7

Hardness Results for Chewy Granola Bars Containing 12% & 15% Allulose After 2 weeks

| Chewy Granola Bar Formulations | Average Hardness (g force) 2 weeks |
|---|---|
| Example 1A | 6,219 ± 706 |
| Example 1G | 4,674 ± 627 |
| Example 1H | 6,262 ± 546 |
| Example 1I | 5,683 ± 490 |
| Example 1J | 5,159 ± 977 |
| Example 1K | 5,538 ± 740 |
| Example 1L | 5,362 ± 610 |

Table 8 shows the percent calorie and sugar reduction for the 5% and 10% allulose containing chewy bar formulations. Calorie reductions of around 5% and 10% were achieved using 5% and 10% allulose, respectively in the chewy granola bar formulation. Sugar reduction ranged from 9.5% to 33.3%; additional sugar reduction was achieved by using low sugar syrup rather than 42 DE corn syrup. The sugar reduction did not include allulose as sugar content.

TABLE 8

Percent Calorie and Sugar Reduction for Chewy Granola Bar Formulations Containing 5% and 10% Allulose

| | Example 1A | Example 1B | Example 1C | Example 1D | Example 1E | Example 1F |
|---|---|---|---|---|---|---|
| Calories (kcal/100 g) | 368 | 350 | 350 | 332 | 332 | 332 |
| Calorie Reduction (%) | NA | 4.9 | 4.9 | 9.8 | 9.8 | 9.8 |
| Sugars (g/100 g) | 21 | 19 | 17 | 17 | 16 | 14 |
| Sugar Reduction (%) | NA | 9.5 | 19.0 | 19.0 | 23.8 | 33.3 |

Table 9 shows the percent calorie and sugar reduction for the 12% and 15% allulose containing chewy bar formulations. Calorie reductions from 12% to 17% were achieved using 12% and 15% allulose, respectively in the chewy granola bar formulation. Sugar reduction ranged from 28.6% to 33.3%.

TABLE 9

% Calorie and Sugar Reduction for Chewy Granola Bar Formulations Containing 12% & 15% Allulose

|  | Example 1G | Example 1H | Example 1I | Example 1J | Example 1K | Example 1L |
|---|---|---|---|---|---|---|
| Calories (kcal/100 g) | 323 | 322 | 323 | 319 | 310 | 306 |
| Calorie Reduction (%) | 12.2 | 12.5 | 12.2 | 13.3 | 15.8 | 16.8 |
| Sugars (g/100 g) | 14 | 14 | 14 | 15 | 14 | 14 |
| Sugar Reduction (%) | 33.3 | 33.3 | 33.3 | 28.6 | 33.3 | 33.3 |

Table 10 shows water activity results for chewy granola bars prepared with 5%, 10%, 12% and 15% allulose. Chewy granola bar water activity results were lower for the all allulose containing bars versus the full sugar control. Replacing the 10 DE Maltodextrin with LSS in the 15% allulose bar further reduced the water activity.

TABLE 10

Water Activity Results for Chewy Granola Bar Formulations With 5%, 10%, 12% and 15% Allulose

| Chewy Granola Bar Formulations | Average Water Activity (2 weeks) |
|---|---|
| Example 1A | 0.61 ± 0.0029 |
| Example 1B | 0.56 ± 0.0025 |
| Example 1D | 0.53 ± 0.0037 |
| Example 1C | 0.57 ± 0.0025 |
| Example 1E | 0.53 ± 0.0034 |
| Example 1F | 0.53 ± 0.0055 |
| Example 1G | 0.50 ± 0.0026 |
| Example 1H | 0.51 ± 0.0064 |
| Example 1I | 0.51 ± 0.0042 |

TABLE 10

Water Activity Results for Chewy Granola Bar Formulations With 5%, 10%, 12% and 15% Allulose

| Chewy Granola Bar Formulations | Average Water Activity (2 weeks) |
|---|---|
| Example 1J | 0.50 ± 0.0020 |
| Example 1K | 0.51 ± 0.0052 |
| Example 1L | 0.47 ± 0.0059 |

Texture evaluation of the chewy granola bars was also conducted by a highly trained sensory panel (n=11). The intensity of firmness was measured using a 0-15 point Universal Scale with industry standard references to anchor the panelists. Data was collected in replicate and the means in the table below represent the means across replicates and panelists. As shown in Table 11, the addition of allulose resulted in a decrease in the firmness texture evaluation score. However, the addition of the LSS increased the firmness scores for both the 5% and 10% allulose bars.

TABLE 11

Sensory Evaluation Results for Chewy Granola Bars

| Attribute | Example 1A | Example 1B | Example 1C | Example 1D | Example 1E | Example 1F |
|---|---|---|---|---|---|---|
| Firmness | 8.95 | 5.68 | 7.32 | 5.18 | 4.9 | 6.55 |

The results in Table 11 also confirm that as allulose content increased, the perceived sensorial firmness went down (8.95 in full sugar control to 5.68 at 5% allulose level and 5.18 at 10% allulose level). Formulating with LSS together with allulose moved the firmness quality towards that of full sugar Control.

Example 2

Making and Analyzing High Protein Bars Employing a Binding Bar Syrup Composition High protein bars were prepared by cooking each binding syrup to 78.0° Brix and combining with the dry ingredients. Bars were molded and cut into 3×10 cm pieces. Similar to the testing for the chewy granola bars in Example 1, water activity and texture (hardness) were measured using the same methods listed before.

Table 12 shows high protein bar formulations containing 10% allulose (dry basis). The Control high protein bar formulation contained standard 62 DE corn syrup and is set forth as Example 2A. 10% Allulose replaced a portion of the 62 DE corn syrup in the high protein bar formulation set forth as Example 2B. Low sugar syrup and 10% allulose replaced a portion of the 62 DE corn syrup in the high protein bar formulation set forth as Example 2C. 10% Allulose and 42 DE corn syrup were used to replace 62 DE corn syrup to improve the binding properties and the texture of the high protein bar formulation set forth as Example 2D.

TABLE 12

High Protein Bar Formulations With 10% Allulose

| | Ingredients | 62 DE Corn Syrup Control Ex. 2A % | 10% Allulose + 62 DE Corn Syrup Ex. 2B % | 10% Allulose + 62 DE Corn Syrup + LSS Ex. 2C % | 10% Allulose + 42 DE Corn Syrup Ex. 2D % |
|---|---|---|---|---|---|
| Dry Ingredients | Milk Protein Isolate | 16.97 | 16.97 | 16.97 | 16.97 |
| | Whey Protein Isolate | 14.87 | 14.87 | 14.87 | 14.87 |
| | Cocoa Powder, alkalized | 5.50 | 5.50 | 5.50 | 5.50 |
| Binder Ingredients | 62 DE Corn Syrup | 42.58 | 30.35 | 15.18 | — |
| | 42 DE Corn Syrup | — | — | — | 30.85 |
| | LSS | — | — | 15.72 | — |
| | Liquid Allulose | — | 13.51 | 13.51 | 13.51 |
| | Water | 6.93 | 5.63 | 5.10 | 5.14 |
| | Glycerin | 4.50 | 4.50 | 4.500 | 4.50 |
| | Almond Butter | 4.09 | 4.09 | 4.09 | 4.09 |
| | Chocolate Liquor | 2.00 | 2.00 | 2.00 | 2.00 |
| | Stevia Sweetener | 0.08 | 0.08 | 0.08 | 0.08 |
| Flavoring | Salt | 0.50 | 0.50 | 0.50 | 0.50 |
| | Natural Chocolate Flavor | 1.50 | 1.50 | 1.50 | 1.50 |
| | Vanilla Extract | 0.50 | 0.50 | 0.50 | 0.50 |
| Totals | | 100 | 100 | 100 | 100 |

Even though it was possible to make a bar in accordance with the Example 2B high protein bar formulation, this bar did not hold its shape during storage and the pieces got stuck to each other and the packaging. It was not possible to conduct texture or sensory analysis of the bar made in accordance with the Example 2B high protein bar formulation, as it was nearly impossible to separate the pieces from each other, again demonstrating the challenge of using allulose directly in bar applications.

Table 13 shows the DP distribution for the binding syrup ingredients used in the high protein bar. Allulose consists primarily of monosaccharides (DP1), whereas DP1+DP2 content of 62 DE Corn Syrup, 42 DE Corn Syrup, and Low Sugar Syrup is about 71%, 34% and 16%, respectively.

TABLE 13

DP results for 62 DE Corn Syrup, 42 DE Corn Syrup, Low Sugar Syrup and Liquid Allulose (dry basis)

| | DP Distribution (% area) | | |
|---|---|---|---|
| Ingredient | DP1 | DP2 | DP3+ |
| 62 DE Corn Syrup | 29.0 | 42.0 | 29.0 |
| 42 DE Corn Syrup | 20.2 | 13.9 | 65.9 |
| Low Sugar Syrup | 4.9 | 11.0 | 84.1 |
| Liquid Allulose | 99.8 | 0.1 | 0.1 |

Tables 14A-14B show the DP1, DP2 and DP3+ content of the bar binding syrups used in the high protein bar formulations set forth in Examples 2A-2D. The higher DP1 content of the bar binder syrup used in the Example 2B high protein bar formulation caused the bar to deform and lose its shape. The lower DP2 content in the bar binder syrup used in the Example 2C high protein bar formulation provided increased stability.

TABLE 14A

DP1, DP2 & DP3+ Content in Bar Binder Syrups Contained in High Protein Bar Formulations

| Bar Binder Syrup | DP1 (% db) | DP2 (% db) | DP1 + DP2 (% db) | DP3+ (% db) |
|---|---|---|---|---|
| Example 2A | 10.10 | 14.63 | 24.73 | 10.10 |
| Example 2B | 17.19 | 10.43 | 27.63 | 7.20 |
| Example 2C | 14.20 | 6.57 | 20.77 | 14.05 |
| Example 2D | 15.01 | 3.45 | 18.47 | 16.37 |

TABLE 14B

Converted DP Content Into % of Binding Syrup

| Bar Binder Syrup | DP1 (%) | DP2 (%) | DP1 + DP2 (%) | DP3+ (%) |
|---|---|---|---|---|
| Example 2A | 29.00 | 42.00 | 71.00 | 29.00 |
| Example 2B | 49.38 | 29.95 | 79.33 | 20.67 |
| Example 2C | 40.77 | 18.86 | 59.63 | 40.34 |
| Example 2D | 43.10 | 9.90 | 53.03 | 47.00 |

Table 15 shows hardness results for the high protein bar formulations of Examples 2A and 2C-2D. The formulation adjusted bars with 10% allulose turned out to be slightly firmer than the Control. So even though the Example 2B bars did not hold their shape, the adjusted formulations with LSS or 42DE corn syrup enabled a high protein bar comparable to the Example 2A control to be made.

TABLE 15

Hardness Results for High Protein Bars Containing 10% Allulose

| High Protein Bar Formulations | Average hardness (g force) (2 weeks) |
|---|---|
| Example 2A | 5,508 ± 719 |
| Example 2C | 7,579 ± 742 |
| Example 2D | 8,359 ± 570 |

Table 16 shows the percent calorie and sugar reduction for the high protein bar formulations of Examples 2A-2D. 10% Allulose formulations reduced calories by about 11%-12% versus the Control. Replacing a portion of the 62 DE corn syrup with allulose reduced sugar by about 31%. Using LSS and 42 DE corn syrup further reduced sugar by about 54%-65%. Consistent with Example 1, the sugar reduction did not include allulose as sugar content.

TABLE 16

% Calorie and Sugar Reduction for High Protein Bar Formulations

| Calorie & Sugar Reduction | Example 2A | Example 2B | Example 2C | Example 2D |
|---|---|---|---|---|
| Calories (kcal/100 g) | 322 | 286 | 286 | 283 |
| Calorie Reduction (%) | NA | 11.2 | 11.2 | 12.1 |
| Sugars (g/100 g) | 26 | 18 | 12 | 9 |
| Sugar Reduction (%) | NA | 30.8 | 53.8 | 65.4 |

Table 17 shows water activity results for the high protein bar formulations of Examples 2A-2D. Unlike the chewy granola bars, no notable differences observed between allulose containing samples and the full sugar sample.

TABLE 17

Water Activity Results for High Protein Bar Formulations

| High Protein Bar Formulations | Average Water Activity (2 weeks) |
|---|---|
| Example 2A | 0.50 ± 0.0026 |
| Example 2C | 0.51 ± 0.0043 |
| Example 2D | 0.52 ± 0.0113 |

Texture evaluation of the high protein bar formulations was conducted by a trained sensory panel. Intensity of firmness was measured using the 15 point Universal Scale as described in Example 1. The Example 2B high protein bar formulation was removed from the sensory analysis because it did hold its shape during storage, with the pieces getting stuck to each other and the packaging.

TABLE 18

Sensory Evaluation Results for High Protein Bar Formulations

| Attribute | Example 2A | Example 2C | Example 2D |
|---|---|---|---|
| Firmness | 6.9 | 7.8 | 8.6 |

Table 18 also shows that even though allulose by itself forms binding and stability problems in high protein bars, complimentarily formulating with LSS or switching the binder syrup to a 42 DE corn syrup helps with generating the bars with acceptable/comparable texture to control.

Example 3

Comparing the Performance of Bar Binder Syrups According to the Invention to Prior Art Bar Binder Syrups Testing was conducted to compare the performance of a food product composition containing a bar binder syrup composition described herein to the dough bar compositions described in US Patent Application Publication No. 2016/0331014 (hereinafter "'014 publication"). The dough bars were reproduced and the texture of the dough bars was measured using the following methods.

Dough bar formulations utilized in the examples set forth in the '014 publication are listed in Table 19 below. The allulose product used in the examples of the '014 publication was composed of 55% allulose and 45% fructose, and at 82% dry solids. The liquid allulose tested in Examples 1 and 2 has a dry solids content of 74% and a 95% allulose purity. The '014 publication used 54.5% allulose syrup having 25% allulose and 20% fructose (54.5*0.82*0.55=25% allulose+54.5*0.82*0.45=20% fructose).

In Table 19 below, the Example 3A formulation used 54.5% Liquid allulose with 74% solids and 95% purity (54.5*0.74*0.95=38% allulose); the Example 3B formulation used an adjusted allulose content of 25% (35.6*0.74*0.95=25% allulose), with 19% crystalline fructose added thereto to generate a composition equivalent to that of the example set forth in the '014 publication; the Example 3C Formulation used 25% allulose+19% LSS used in Example 1 to represent a binding bar syrup composition according to the invention; the Example 3D formulation used approximately one half of the 54.5% allulose syrup as liquid allulose (27.25%)+the remaining one half as LSS used in Example 1 (27.5%); and the Example 3E and 3F formulations were parallel formulations that used other ingredients similar to those used in the examples of the '014 publication, i.e. HYSTAR® 5875 was used instead of Polysorb® 75/67 (similar % dry solids, both 75%; and comparable maltitol contents-HYSTAR® 5875 has around 60% maltitol, Polysorb® 75/67 has around 67% maltitol).

The binding syrups were heated to 75° C. as described in the '014 publication. As noted at the bottom of Table 19, heating syrups with different dry solids up to a certain temperature (75° C. in this case) results in different Brix values in the binder syrups (this would apply to any bar formulation). According to the methods of the invention, it is preferred to make bars by heating the binder bar syrup composition to a certain Brix (independent of temperature), such as described in Examples 1 and 2. However, in an effort to replicate the examples set forth in the '014 publication, the same heating method was used here as in the '014 publication. After reaching 75° C., the binding syrups were combined with the dry ingredients and mixed in a Hobart mixer to form a dough ball. The dough balls were formed into a slab and cut into 3×10 cm pieces (the size of the pieces was not specified in the example set forth in the '014 publication). Dough bars were stored in clamshell containers and placed in metallized bags.

Example 3A showed comparable hardness and hardening rate at 1.5 months to the allulose containing bar of the '014 publication (Table 20); however, it was very sticky and did not form well. Higher solids in Example 3B (final syrup 79.5 Brix) resulted in a harder bar than Example 3A (final syrup 72.0 Brix) at Day 1, and it was also sticky, but had a more

TABLE 19

Dough Bar Formulations

| | Ingredients | Allulose (38%) Ex. 3A | Allulose (25%) + Fructose (19%) Ex. 3B | Allulose (25%) + LSS (19%) Ex. 3C | Allulose (19%) + LSS Ex. 3D | 63 DE Corn Syrup + HFCS 42 Ex. 3E | HYSTAR ® 5875 Ex. 3F |
|---|---|---|---|---|---|---|---|
| Dry Ingredients | Nutralys ® Pea Protein 58F | 18.20 | 18.20 | 18.20 | 18.20 | 18.20 | 18.20 |
| | Whey Protein Concentrate 515 Fonterra 111762 | 18.20 | 18.20 | 18.20 | 18.20 | 18.20 | 18.20 |
| | Nutriose ® FM06 | 7.30 | 7.30 | 7.30 | 7.30 | 7.30 | 7.30 |
| Binder Ingredients | Liquid Allulose with 95% purity and at 74% solids | 54.50 | 35.60 | 35.60 | 27.25 | 0 | 0 |
| | LSS | 0 | 0 | 18.90 | 27.25 | 0 | 0 |
| | 63 DE Corn Syrup | 0 | 0 | 0 | 0 | 27.25 | 0 |
| | High Fructose Corn Syrup (HFCS) 42 | 0 | 0 | 0 | 0 | 27.25 | 0 |
| | HYSTAR ® 5875 | 0 | 0 | 0 | 0 | 0 | 54.50 |
| | Crystalline Fructose Now Real Food | 0 | 18.90 | 0 | 0 | 0 | 0 |
| | Canola Oil | 1.80 | 1.80 | 1.80 | 1.80 | 1.80 | 1.80 |
| Totals | | 100 | 100 | 100 | 100 | 100 | 100 |
| Final Syrup Brix | | 72.0 | 79.5 | 76.5 | 79.0 | 76.5 | 79.0 |

Bar hardness was assessed using texture analysis (Stable Micro Systems TAXT2 Texture Analyzer). Both CHOC2/P4 (the method mentioned in the '014 publication) and bar cut test texture analysis methods (the method used in Examples 1 and 2 above) were used. Hardness was measured at 1 day, 7 days and 1.5 months according to the example in the '014 publication. Water activity of the bars was also measured; methodology and results as described in Examples 1 and 2 above.

Figure 1:
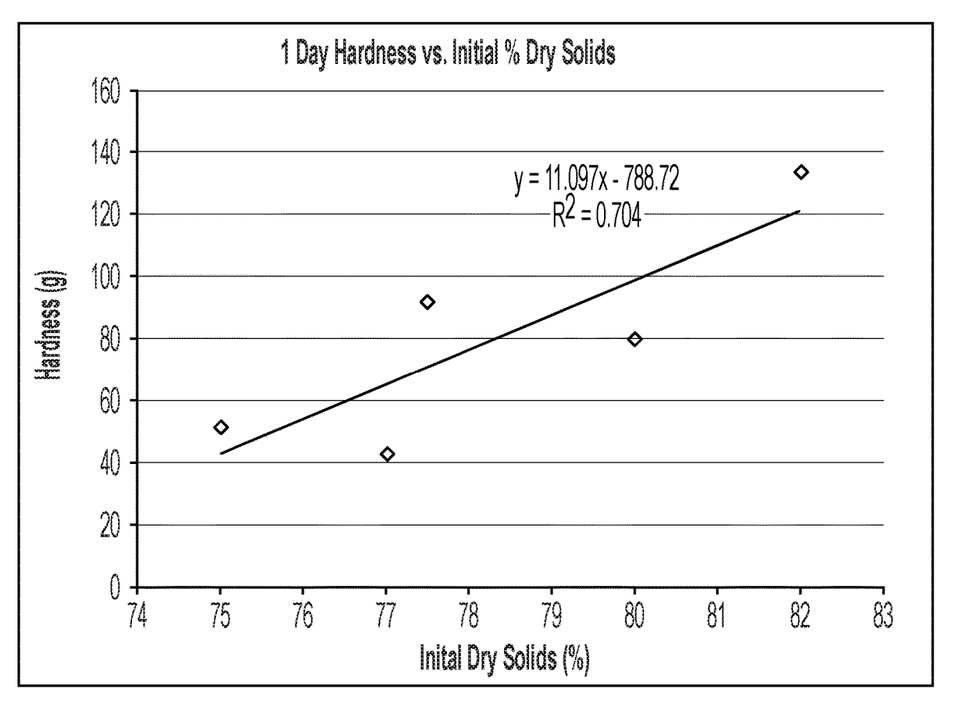
FIG. 1 shows measurements of hardness versus initial percentage of dry solids for compositions evaluated in Example 3.

Table 20 shows texture analysis results using the CHOC2/P4 method referenced in the '014 publication, which method is incorporated herein by reference in its entirety. The '014 publication states that dough bars made with allulose provided both enough hardness (i.e. more than 90 g) after manufacture and a slow hardening (i.e. less than 300%) over 1.5 months compared to the other bars made in the example.

defined shape due to its higher solids content (FIG. 1). The hardening rate of Example 3B at Day 7 was only 5%. Overall, both Example 3A (just allulose at 38%) and Example 3B (allulose+fructose together) were the softest of all the bars prepared and not very well formed. This is in agreement with data in Examples 1 and 2 above.

In the formulations of Example 3C and 3D, using the combination of Allulose+LSS resulted in bars that were not sticky, and exhibited a more defined bar shape. The hardness was also higher and more as desired, and the rate of hardening was slower compared to the allulose containing bar of the '014 publication and the formulation of Example 3A. Overall bars were less sticky than the allulose containing bars and held their shape better.

The Example 3E and 3F bar formulations were less sticky than the Example 3A and 3B bar formulations, and held their shape better, similar to the Examples 3C and 3D bar for-

TABLE 20

Dough Bar Texture Analysis Results Using CHOC2/P4 Method

| | Average Hardness (g) [hardening rate] | | |
|---|---|---|---|
| Dough Bar Formulation | Day 1 | Day 7 | 1.5 Months |
| Ex. 2 from '014 publication (Allulose (25%) + Fructose (20%)) | 134 | 328 [145%] | 521 [289%] |
| Example 3A | 120 ± 7.8 | 253 ± 8.3 [111%] | 511 ± 22.6 [326%] |
| Example 3B | 260 ± 36.2 | 274 ± 33.1 [5%] | 329 ± 36.1 [27%] |
| Example 3C | 632 ± 45.3 | 924 ± 46.0 [46%] | 1,655 ± 99.5 [162%] |
| Example 3D | 1,268 ± 135.0 | 1,698 ± 135.6 [34%] | 2,763 ± 145.7 [118%] |
| Ex. 2 from '014 publication (63 DE CS + HiSweet ® 42) | 92 | 206 [124%] | 665 [622%] |
| Example 3E | 705 ± 76.2 | 726 ± 92.7 [3%] | 1,198 ± 78.1 [70%] |
| Ex. 2 from '014 publication (Polysorb ® 75/67) | 52 | 91 [75%] | 250 [381%] |
| Example 3F | 875 ± 60.5 | 939 ± 123.0 [7%] | 1,047 ± 113.3 [20%] | mulations. The hardness values of the Example 3E and 3F bar formulations were much higher than their bar counterparts set forth in the '014 publication, but were more in alignment with the Example 3C and 3D bar formulations. Hardening rates for the Example 3E and 3F bar formulations were also notably slower than their bar counterparts set forth in the '014 publication. All of the bars prepared in Example 3 provided more sufficient hardness values, and slower hardening rate compared to the allulose containing bars set forth in the examples of the '014 publication.

Hardness by 'Bar Cut' Texture Analysis Methods were also completed. Bar cut hardness results are shown in Table 21. Similar trends between samples were observed as in the other texture analysis method (Table 20).

TABLE 21

Dough Bar Texture Analysis Results Using Bar Cut Test Method

| | Average Hardness (g) [hardening rate] | | |
|---|---|---|---|
| Dough Bar | Day 1 | Day 7 | 1.5 Months |
| Example 3A | 1,898 ± 283 | 3,588 ± 832 [89%] | 5,899 ± 443 [211%] |
| Example 3B | 2,209 ± 174 | 2,530 ± 315 [15%] | 2,555 ± 423 [16%] |
| Example 3C | 6,821 ± 669 | 8,042 ± 660 [18%] | 13,500 ± 1,210 [98%] |
| Example 3D | 14,497 ± 1,319 | 16,353 ± 1,708 [13%] | 26,016 ± 1,380 [80%] |
| Example 3E | 8,475 ± 1,318 | 7,442 ± 720 [12%] | 9,783 ± 883 [15%] |
| Example 3F | 8,991 ± 1,783 | 8,806 ± 1,411 [2%] | 9,360 ± 1,052 [4%] | types of bars. Allulose+LSS bars also hardened at a slower rate after 7 days compared to Allulose control, confirmed by two different texture analysis methods. No differences in hydration of the dry ingredients and/or the time necessary to make the dough bars were observed between allulose and the other syrup ingredients (all dough bars were prepared the same way).

The way the bars were prepared in the '014 publication by cooking to a certain temperature rather than a certain Brix is not typically used especially given the various percent solids in the syrups tested. To illustrate this further, FIG. 1 is generated from the example set forth in the '014 publication to show the general trend of increasing bar hardness with increasing initial dry solids of the binder syrup (where the binder syrup is heated to a certain temperature without regard for Brix value). As shown in FIG. 1 and Table 22, one of the reasons the Allulose bar was shown to be the hardest was due to having the highest initial % dry solids content. The other bars would have achieved different hardness levels if their binding syrups were heated to a similar Brix level, instead of the same final temperature (75° C.). Brix of the final syrup is not the only factor affecting the hardness, chemical structure/composition (carbohydrate distribution) would have an effect as well.

TABLE 22

Initial Percent Dry Solids versus Bar Hardness (Day 1)

| Ingredient | Initial Dry Solids (%) | CHOC2/P4 1 Day Bar Hardness (g) |
|---|---|---|
| Allulose | 82 (examples in '014 publication) | 134 |
| Lycasin ® 80-55 | 80 (examples in '014 publication) | 80 |
| 63 DE Corn Syrup + Hi Sweet ® 42 | 77.5 (approximately calculated) | 92 |
| Hi Sweet ® 55 | 77 (typical HFCS 55) | 43 |
| Polysorb ® 75/67 | 75 (examples in '014 publication) | 52 |

Overall conclusions of the testing show that using the combination of Allulose+LSS in the protein dough bars resulted in bars that were not sticky, had a well-defined shape, and were easier to mold than bars with just allulose as demonstrated in Examples 1 and 2 hereinabove, even when the formulation in the '014 publication was used. Allulose+LSS bars exhibited comparable hardness and water activity values compared to 63 DE corn syrup+HFCS 42 and HYSTAR® 5875, which can be counted as commercial benchmarks as these ingredients are used in various Water activity of the bars was measured using a Rotronic HygroLab3 at 1 day, 7 days and 1.5 months according to the examples set forth in the '014 publication. The method included: Loading analysis cup to halfway line with crumbled bar pieces; and Recording average of 4 replicates. Table 23 shows water activity results for the dough bars did not change drastically over time. The addition of fructose drastically lowered the water activity, which was unexpected and beneficially correlates to improved shelf-life stability by inhibiting microbial growth.

TABLE 23

Dough Bar Water Activity Results

| Dough Bar | Average Water Activity | | |
|---|---|---|---|
| | Day 1 | Day 7 | 1.5 Months |
| Example 3A | 0.57 | 0.58 | 0.56 |
| Example 3B | 0.42 | 0.40 | 0.45 |
| Example 3C | 0.54 | 0.52 | 0.59 |
| Example 3D | 0.55 | 0.58 | 0.58 |
| Example 3E | 0.56 | 0.56 | 0.55 |
| Example 3F | 0.57 | 0.56 | 0.56 |

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims. The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A binding bar syrup composition comprising:
    allulose in an amount from about 15% to about 37.5% (wt. %) of the binding bar syrup;
    at least one low sugar syrup having low mono- and di-saccharide content; optionally, an additional syrup; and,
    at least one additional binder ingredient one or more additional binder ingredients selected from the group consisting of water, glycerin, nut butters, flavorings extracts, flavoring liquor, salt, fats, oils, maltodextrin, polydextrose, xanthan gum, guar gum, soluble corn fiber, polyols wherein the combination of one or more additional binder ingredients are in an amount, or from about 12.5 wt-% and about 50 wt-% of the binding bar syrup;
    wherein the binding bar syrup composition has a DP1+DP2 content from the at least one low sugar syrup and optional additional syrup in an amount from about 8% to about 15% (wt. % of the binding bar syrup) and DP 3+ content greater than about 35% (wt. %) and wherein the binding bar syrup a DP1 to DP3+ content ratio is less than about 2.0;
    wherein the binding bar syrup has a Brix of at least 80° Brix
    wherein the composition does not include sucrose.

2. The binding bar syrup of claim 1 wherein the low sugar syrup has a total DP1 and DP2 content of less than about 25%.

3. The composition according to claim 1, wherein the allulose is a liquid syrup comprising at least about 85% allulose and about 15% other monosaccharides and/or disaccharides.

4. A food product composition comprising: the binding bar syrup composition according to claim 1; dry ingredients; and, optionally, additional binder ingredients, wherein the composition is a bar.

5. The food product composition according to claim 4, comprising from about 5 wt-% to about 20 wt-% allulose, and from about 5 wt-% to about 20 wt-% of the low sugar syrup.

6. The food product composition according to claim 4, wherein the dry ingredients comprise one or more of oat, rice, barley, dried fruit, nuts, protein isolate, spices, vegetable and vegetable-derived products, legumes and legume-derived products, starch-based ingredients, proteins, cocoa powder, chocolate chips, dietary fibers, and protein crisps.

7. The food product composition according to claim 4, wherein the additional binder ingredients comprise at least one of water, glycerin, nut butter, flavorings and/or extracts, flavoring liquor, salt, fat, oil, bulking agents, polyols and additional co-sweeteners.

8. The food product composition according to claim 4, wherein the composition is free of at least one of water, glycerin, and sucrose.

9. The food product composition according to claim 4, wherein the binding bar syrup comprises between about 35 wt-% to about 65 wt-% of the composition and the dry ingredients comprise between about 35 wt-% to about 65 wt-% of the composition.

10. The food product composition according to claim 4, wherein the bar is a granola bar, snack bar, high protein bar, high fiber bar, sports nutrition bar, energy bar, recovery bar, confectionery bar, or breakfast bar.

11. The food product composition according to claim 4, wherein the 2 week measured hardness of the bar (grams force) is at least equivalent or greater than a full sugar control formulation, or at least about 6,000 g force at 2 weeks.

12. A method of making a food product composition comprising:
    combining the binding bar syrup composition according to claim 1 with dry ingredients; blending to form a substantially homogenous food product composition;
    molding to form a food product composition in the form of a bar; and, optionally, cutting the molded bar food product composition.

13. The method according to claim 12, wherein the bar is a granola bar, snack bar, high protein bar, high fiber bar, sports nutrition bar, energy bar, recovery bar, confectionery bar, or breakfast bar.

14. The method according to claim 12, wherein the binding bar syrup composition comprises between about 35 wt-% to about 65 wt-% of the composition and the dry ingredients comprise between about 35 wt-% to about 65 wt-% of the composition.

* * * * *